United States Patent
Chuang et al.

[11] Patent Number: 6,137,570
[45] Date of Patent: Oct. 24, 2000

[54] SYSTEM AND METHOD FOR ANALYZING TOPOLOGICAL FEATURES ON A SURFACE

[75] Inventors: Yung-Ho Chuang, Cupertino; J. Joseph Armstrong, Milpitas; David L. Brown, Sunnyvale; Jason Z. Lin; Bin-Ming Benjamin Tsai, both of Saratoga, all of Calif.

[73] Assignee: KLA-Tencor Corporation, San Jose, Calif.

[21] Appl. No.: 09/107,391

[22] Filed: Jun. 30, 1998

[51] Int. Cl.⁷ .................................................. G01N 21/00
[52] U.S. Cl. .................................. 356/237.5; 356/237.2; 250/559.04
[58] Field of Search ............................ 356/237.1, 237.2, 356/237.5, 237.3, 237.4; 250/559.04

[56] References Cited

U.S. PATENT DOCUMENTS

| | | | |
|---|---|---|---|
| 4,247,203 | 1/1981 | Levy et al. ................................. | 356/398 |
| 4,347,001 | 8/1982 | Levy et al. ................................. | 356/398 |
| 4,360,269 | 11/1982 | Iwamoto et al. .......................... | 356/239 |
| 4,448,532 | 5/1984 | Joseph et al. ............................. | 356/394 |
| 4,579,455 | 4/1986 | Levy et al. ................................. | 356/394 |
| 4,595,289 | 6/1986 | Feldman et al. .......................... | 356/237 |
| 4,778,745 | 10/1988 | Leung ....................................... | 430/311 |
| 4,806,774 | 2/1989 | Lin et al. .................................. | 250/550 |
| 4,926,489 | 5/1990 | Danielson et al. ........................... | 382/8 |
| 4,996,434 | 2/1991 | Tanaka .................................. | 250/492.3 |
| 5,131,755 | 7/1992 | Chadwick et al. ....................... | 356/394 |
| 5,177,559 | 1/1993 | Batchelder et al. ...................... | 356/237 |
| 5,185,636 | 2/1993 | Button et al. ............................. | 356/73.1 |
| 5,241,369 | 8/1993 | McNeil et al. ........................... | 356/445 |
| 5,270,794 | 12/1993 | Tsuji et al. . | |
| 5,410,400 | 4/1995 | Shishido et al. ......................... | 356/237 |
| 5,428,442 | 6/1995 | Lin et al. .................................. | 356/237 |
| 5,442,189 | 8/1995 | Hagiwara ............................ | 250/559.42 |
| 5,502,306 | 3/1996 | Meisburger et al. .................... | 250/310 |
| 5,502,311 | 3/1996 | Imai et al. ................................. | 250/548 |
| 5,506,676 | 4/1996 | Hendler et al. .......................... | 356/237 |
| 5,513,275 | 4/1996 | Khalij et al. ............................. | 382/149 |
| 5,539,514 | 7/1996 | Shishido et al. ......................... | 356/237 |
| 5,546,181 | 8/1996 | Kobayashi et al. ...................... | 356/237 |
| 5,563,702 | 10/1996 | Emery et al. ............................... | 356/73 |
| 5,572,598 | 11/1996 | Wihl et al. ............................... | 382/144 |
| 5,578,821 | 11/1996 | Meisberger et al. ..................... | 250/310 |
| 5,619,429 | 4/1997 | Aloni et al. .............................. | 364/552 |
| 5,659,390 | 8/1997 | Danko . | |
| 5,825,043 | 10/1998 | Suwa ....................................... | 356/399 |

OTHER PUBLICATIONS

Lifeng Li, "Modal method by Fourier expansion for modeling crossed gratings," Tuscon, Arizona, *Optical Sciences Center*.

Lifeng Li, "New formulation of the Fourier modal method for cross surface–relief gratings," Mar. 31, 1997, Tucson, Arizona, *Optical Sciences Center*.

*Primary Examiner*—Frank G. Font
*Assistant Examiner*—Roy M. Punnoose
*Attorney, Agent, or Firm*—Beyer Weaver & Thomas, LLP

[57] ABSTRACT

Disclosed is a method and apparatus for using far field scattered and diffracted light to determine whether a collection of topological features on a surface (e.g., a semiconductor wafer) conforms to an expected condition or quality. This determination is made by comparing the far field diffraction pattern of a surface under consideration with a corresponding diffraction pattern (a "baseline"). If the baseline diffraction pattern and far field diffraction pattern varies by more than a prescribed amount or in characteristic ways, it is inferred that the surface features are defective. The method may be implemented as a die-to-die comparison of far field diffraction patterns of two dies on a semiconductor wafer. The portion of the far field scattered and diffracted light sensitive to a relevant condition or quality can also be reimaged to obtain an improved signal-to-noise ratio.

29 Claims, 14 Drawing Sheets

Simulated Far-field Pattern

Variation Sensitivity Map

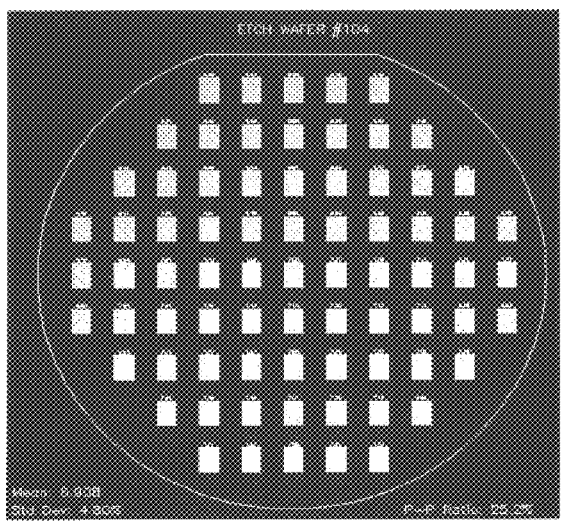 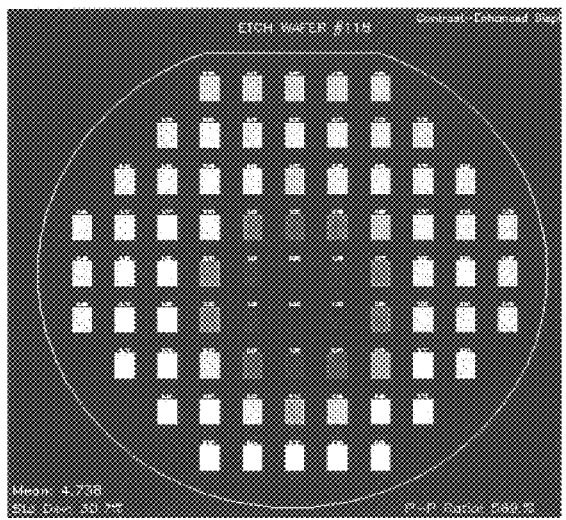
Figure 12a
Figure 12b

SYSTEM AND METHOD FOR ANALYZING TOPOLOGICAL FEATURES ON A SURFACE

BACKGROUND OF THE INVENTION

This invention relates to a method and apparatus for evaluating surface features such as those on a partially fabricated integrated circuit. More specifically, the invention relates to methods and apparatus for using the far-field pattern of scattered and diffracted light from the surface features to evaluate the quality or condition of the features.

Many optical and electronic systems exist for identifying and classifying surface feature errors such as those on a partially fabricated integrated circuit or a reticle. These errors may take the form of particles randomly localized on the surface, scratches, process variations such as under etching, etc. Such techniques and apparatus are well known in the art and are embodied in various commercial products such as many of those available from KLA-Tencor Corporation of San Jose, Calif.

Relatively few techniques are available for evaluating the condition of surface features (e.g., contacts, vias, deep trenches, polysilicon gate structures, reticle features, etc.). Most generally, these surface features may be viewed as design features which show up as topological variations on a surface. Often, one wishes to know whether or not such features (as formed in a conventional process) fall within specified tolerances. For example, the depth, diameter and slope of a contact hole or via should fall within specified tolerances. If a contact hole is etched too deeply, it may cut into the substrate and thereby detrimentally effect the electrical performance of a transistor. An over etched via may cut through an underlying contact to change resistance, etc. If a via is under etched (not sufficiently deep), there may be no contact between an upper level metallization line and a lower level metallization. If a via is etched too narrowly, the current density in the resulting interconnect may be too high, possibly resulting in premature failure.

These and similar problems often arise when processing equipment malfunctions or degrades in performance over time. Examples of such equipment include plasma etchers, deposition systems, chemical mechanical planarization systems, reticle processing, and photolithography equipment. Obviously, a manufacturer needs to know when the process equipment ceases to function in an acceptable manner.

A few techniques do exist for evaluating the condition of topologic features on a reticle or integrated circuit. The simplest of these involves a casual visual inspection by a technician of a wafer held in white light and examined to determine whether there is any variation in the appearance of the various dies fabricated on the wafer. Ideally, each die should have the same appearance when moved about under a white light. If there is any variation in the appearance of one or more of the dies on the wafer, then it can be assumed the dies are not structurally identical and some problem exists. A related technique simply involves performing optical microscopy (e.g., bright field or dark field imaging) on the various dies of a wafer. Any variation in the image of the individual die indicates that there is a problem in at least that die. However, due to the trend of small design rule, high aspect ratio, and the complexity of the background circuit, defective vias or contact holes are at times difficult to detect through standard microscopic methods.

More accurate techniques exist for evaluating surface features. For example, ion milling may be employed to evaluate the condition of a section of an integrated circuit. Ion milling cuts through the circuit creating a cross section at a location of interest, possibly an area where vias are suspected of being defective. Subsequently, a scanning electron micrograph images the cross section. From this, over etching, under etching, defective profiles, etc. in the vias can be visualized. Unfortunately, this technique destroys the integrated circuit.

In some cases, scanning electron microscopy or a similar electron beam technique is employed to image the surface of a die (as opposed to a cross section). While this technique does not necessarily destroy the integrated circuit, the electrons may damage the substrate surface. Further, both ion milling and scanning electron microscopy are currently very slow processes and therefore unsuitable for regular use in the normal process flow of an integrated circuit fabrication facility.

What is needed therefore is a rapid, non-destructive, and inexpensive technique for evaluating non-random topological variations on the surface of a substrate such as a partially fabricated integrated circuit or a reticle.

SUMMARY OF THE INVENTION

The present invention provides a method and apparatus of using far-field scattered and diffracted light to determine whether a collection of topological features on a surface (e.g., a semiconductor wafer) conforms to an expected condition or quality. This determination can be made by comparing the far-field pattern (preferably at or near the Fourier plane) of a surface under consideration with a corresponding far-field pattern (a "baseline"). If the far-field patterns vary by more than a prescribed amount, it is assumed that some aspect of the surface features is defective. In one embodiment, this invention is implemented using a die-to-die comparison of far-field patterns of two or more dies on a semiconductor wafer. The portion of the far-field scattered and diffracted light sensitive to a relevant condition or quality (e.g., etch depth) can also be imaged to obtain an improved signal-to-noise ratio for detecting the condition of interest over so called nuisance defects which do not impact the fabrication process.

One aspect of the present invention provides a method for determining the condition or changes in the condition of surface features defining a pattern on an electronic device. The method may be characterized as including the following sequence: (a) illuminating a region of the surface such that light is scattered and diffracted off surface features; (b) detecting the scattered and diffracted light from the surface features; (c) comparing the far-field pattern of scattered and diffracted light to baseline information; and (d) determining whether the far-field pattern from the first region significantly deviates from the baseline information. Often the method will benefit from selecting the polarization of the illuminating light. Also, the method will often benefit from optically filtering or analyzing the scattered and diffracted light from the features on the surface before detecting the light.

The baseline information may be obtained from a variety of sources. For example, it may be calculated according to a method which predicts a pattern of scattered and diffracted light. Alternatively, it may be measured far-field data taken from light scattered and diffracted off a surface having a known condition. In some instances, the baseline information may be selected from a database which stores a collection of far-field patterns (e.g., patterns for a nominal surface and a plurality of surfaces with vary from a nominal image for the first region).

The scattered and diffracted light that is detected may be any portion of the far-field pattern. In some cases, it will include multiple diffraction orders or regions. In other cases, it will include only one or a few diffraction orders or regions. This depends on what information is required and how much of that information is contained in one or a small group of diffraction orders or particular regions. If a manufacturer is concerned only with changes in the depth of its vias, it may detect only those diffraction orders or regions that vary significantly with depth changes. By limiting detection to only those diffraction orders or regions that contain important information, the signal-to-noise ratio and speed of the method improves.

Another aspect of the invention provides a method for inspecting a single or plurality of openings in a film on a substrate. The method may be characterized as including: (a) illuminating a first portion of the openings; (b) detecting the far-field scattered and diffracted light; (c) illuminating a second portion of the openings, the second portion of the openings having a pattern which is substantially identical to the first portion; (d) detecting far-field scattered and diffracted light produced by the illumination of the second portion; and (e) comparing signals detected from illumination of the first portion with signals detected from illumination of the second portion, thereby determining whether variations exist in the openings.

In one embodiment, the surface is a dielectric layer on a semiconductor wafer and the openings are contact holes or vias in the dielectric layer. In the case of a die-to-die comparison, the first portion is a region of a first die on a semiconductor wafer and the second portion is a region located at the same relative position of a second die on the semiconductor wafer. In the case of die-to-database comparison, the first portion is a die on a semiconductor wafer and the second portion is a stored representation for that location.

Yet another aspect of the invention provides an apparatus for evaluating the condition of topological features on a substrate surface. In this aspect, the apparatus may be characterized as including the following features: (a) a light source arranged to direct light onto the substrate surface such that the light is scattered and diffracted by the substrate surface; (b) a sensor configured to capture and detect a diffraction pattern of the light scattered and diffracted by the substrate surface; and (c) a computer configured to compare the diffraction pattern from the substrate surface with a baseline diffraction pattern of light scattered and diffracted from a baseline surface having a condition corresponding to an expected condition of the substrate surface. Often the apparatus will also require optics aligned to capture light scattered and diffracted from the substrate surface and direct it onto the sensor.

Preferably, the light source is a coherent light source such as a laser. The sensor may be a camera or other detector such as a charge coupled device, CMOS photodiode array, or a single element detector.

The apparatus may include optics to capture light scattered and diffracted from the substrate surface and direct it onto the sensor. In a preferred embodiment, the optics are capable of capturing diffraction angles from normal to near 85 degrees. The optics can also support illumination of the substrate surface at the desired angles. The optics may also be configured to produce a pupil plane that can support Fourier filtering. A Fourier filter or aperture can be used to block or attenuate one or more regions of the diffraction pattern from the substrate surface. The design and orientation of the Fourier filter or aperture allows portions of the diffraction pattern relevant to the problem at hand to pass to the sensor while blocking or attenuating other less relevant portions of the diffraction pattern thereby improving signal-to-noise ratio for detecting changes critical to device fabrication. The apparatus may optionally include other optical elements such as optics comprising a microscope for providing spatial imaging of the substrate surface.

In a preferred embodiment, the apparatus also includes a memory device coupled to the computer or being a component of the computer. The memory device will store at least one baseline diffraction pattern. In a particularly preferred embodiment, the memory device is a database storing a plurality of baseline diffraction patterns for multiple expected conditions of the substrate surface and for different locations on the surface.

The features and advantages of this invention may be further appreciated with reference to the following detailed description and associated drawings.

BRIEF DESCRIPTION OF THE DRAWINGS

FIG. 12a is the result of die-to-die comparisons of a die with known good vias and dies on a wafer with good vias.

FIG. 12b is the result of die-to-die comparisons of a die with known good vias and dies on a wafer with bad vias in the center dies.

DETAILED DESCRIPTION OF THE PREFERRED EMBODIMENTS

Figure 1A:
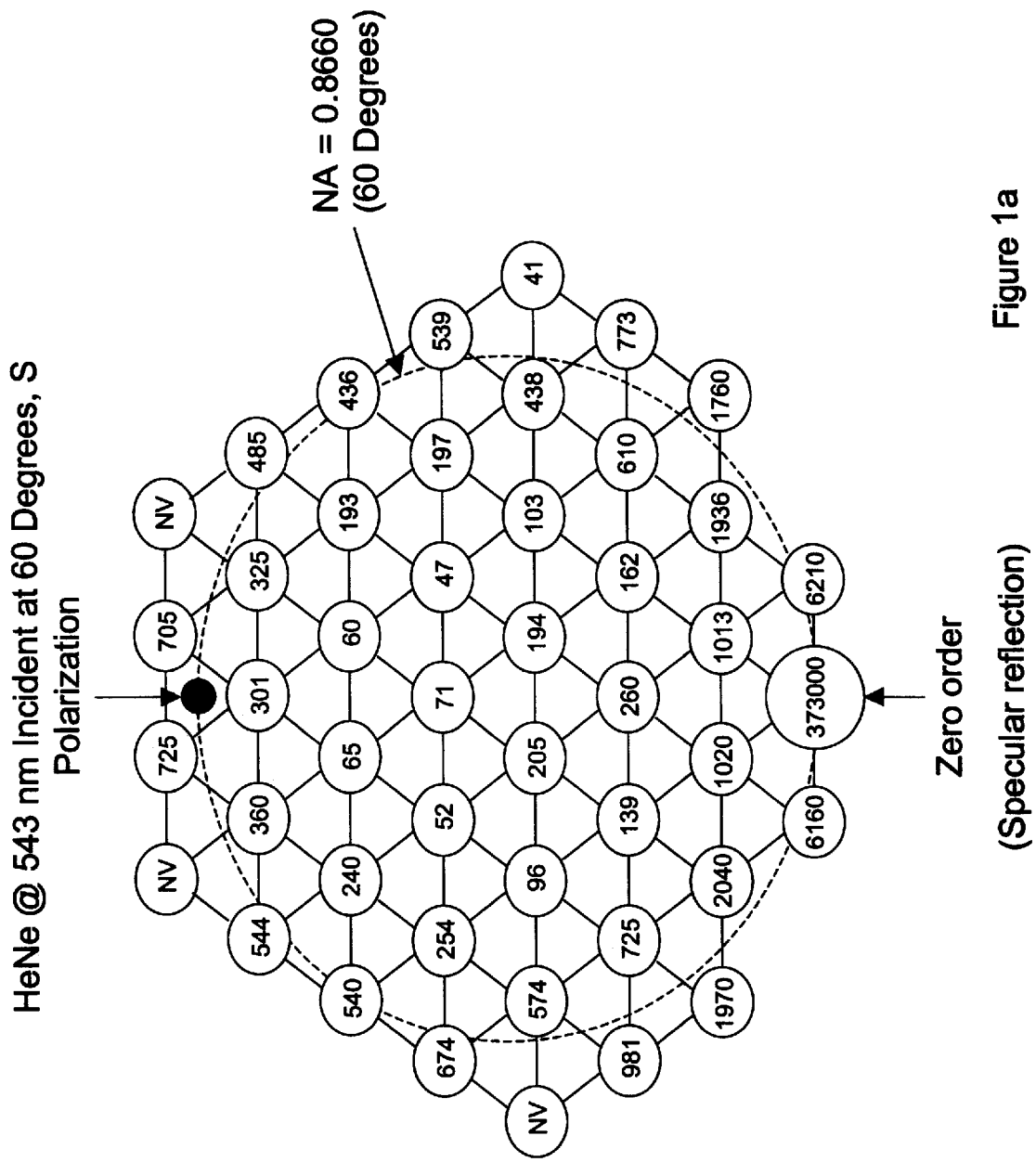
FIG. 1a is a laser diffraction order energy distribution for a properly formed via array.

The present invention provides a method and apparatus for comparing far-field patterns of scattered and diffracted light from surface features to reference far-field information (also referred to as a "baseline" or "baseline information") to identify errors or changes in the surface features. In the following description, numerous specific details are set forth in order to fully illustrate a preferred embodiment of the present invention. It will be apparent, however, that the present invention may be practiced without limitation to some specific details presented herein.

This invention relies upon similarities and differences in the far-field patterns of scattered and diffracted light as evidence of the condition or quality of surface features. For this invention, the term far-field refers to the optical far-field of diffraction theory which is well known to anyone skilled in optics. For light of defined wavelengths, polarization, intensity, and angle of incidence, the far-field patterns of scattered and diffracted light should be identical for two surfaces with identical features. However, if one of the surfaces has features that deviate even slightly, then the far-field patterns of scattered and diffracted light will vary in observable ways. By comparing the far-field pattern of the surface features of interest with real or simulated far-field patterns, one can determine whether the surface has the desired condition or quality.

Scattering arises when light strikes a surface that is not perfectly smooth. Thus, scattering can be caused by a particle on a surface, the edges of a feature, a topological variation on a surface, or material transitions on a surface. If the surface has a repeating collection of similar topological variations, then light incident on that surface will simultaneously scatter or diffract from the multiple topological variations to produce bright and dark regions of constructive and destructive interference in the far-field. For a simple one-dimensional grating surface, the location of the repeating pattern of bright regions or diffraction orders can be easily calculated using the grating equation $m\lambda/d = (\sin\alpha + \sin\beta)$, where $\lambda$ is the wavelength of light incident on the surface, d is the spacing distance of the repeating topological features, m is an integer representing the diffraction order, $\alpha$ is the angle with respect to the surface normal of the incident light, and $\beta$ is the angle with respect to the surface normal where the diffraction order occurs Thus $\beta$ gives the angular location of the diffraction for each order (m). For a surface having more complex two dimensional topological variations it is much more difficult to calculate the resulting far-field pattern. It will be a complex two-dimensional pattern of bright and dark regions. Nevertheless, an arrangement of surface features in two dimensions will produce a characteristic far-field pattern.

Generally, this invention applies to detecting errors in any surface features that produce a far-field pattern by scattering and diffracting incident illumination. Errors in the surface features will redistribute the intensity, phase, and polarization of the far-field pattern. In some cases, very small errors in surface features will give rise to large changes the far-field pattern.

Examining the condition or quality of surface features by using far-field scattered and diffracted light has several advantages over using traditional bright-field imaging. Bright field imaging can only detect surface features that are within the resolution limit of the imaging system. For the case of a high resolution imaging system, the resolution limit is about half the wavelength of the illuminating light. However, by using light that is scattered and diffracted into the far-field, features and particles smaller than half the wavelength of the illuminating light can be detected. Bright field imaging also has limited sensitivity for detecting variations in the depth of small, high aspect ratio structures such as contacts, vias, and deep trenches. However, far-field scattered and diffracted light is very sensitive to changes in the depth of high aspect ratio surface features. Even small depth changes of 0.5 nm can be detected by examining the far-field pattern. An additional advantage is that in conventional bright field imaging there is a one-to-one mapping between the inspected surface locations and the collected image. However, in the far-field, certain features from a large region or zone on the inspected surface may map to a single location. This feature can be used to perform very high speed inspection while retaining high sensitivity to process changes affecting multiple surface features.

In the electronics industry, many surfaces possess non-random topological features or material combinations that will generate a far-field pattern that can be evaluated to determine the condition of surface features. The following examples discuss detecting errors in openings (vias and contact holes) in a film. However, there are many other examples from the electronics industry that can be evaluated with the methods and apparatus of this invention. These include deep trenches in a semiconductor substrate or surface film, field oxide regions, patterned photoresists, metal or polysilicon layers, damascene layers, etc. Beyond semiconductor wafer and die surfaces, this invention may be applied to image reticles, phase shift masks, X-ray masks, and other structures having non-random surface features in two-dimensions.

For the case of an opening in a surface or surface film, this invention may evaluate various parameters characterizing such openings. For example, the invention may detect variations in opening diameter, depth, and angle. Thus, it may detect whether a via or contact is over etched, under etched, too wide, too narrow, too conical, angled too far from the surface normal, etc. It may also detect the presence of residue left in such openings.

While the interaction of surface parameters (e.g., via depth, width, and angle) and illuminating light is a very complex problem, some generalizations may apply to the scattered and diffracted light in certain systems. For example, high angle scattering and diffraction may provide the most information about the depth of the openings and the shape of the bottom of the openings (to allow identification of residue in the via for example). Such associations may be obtained experimentally for a given system.

Figure 1B:
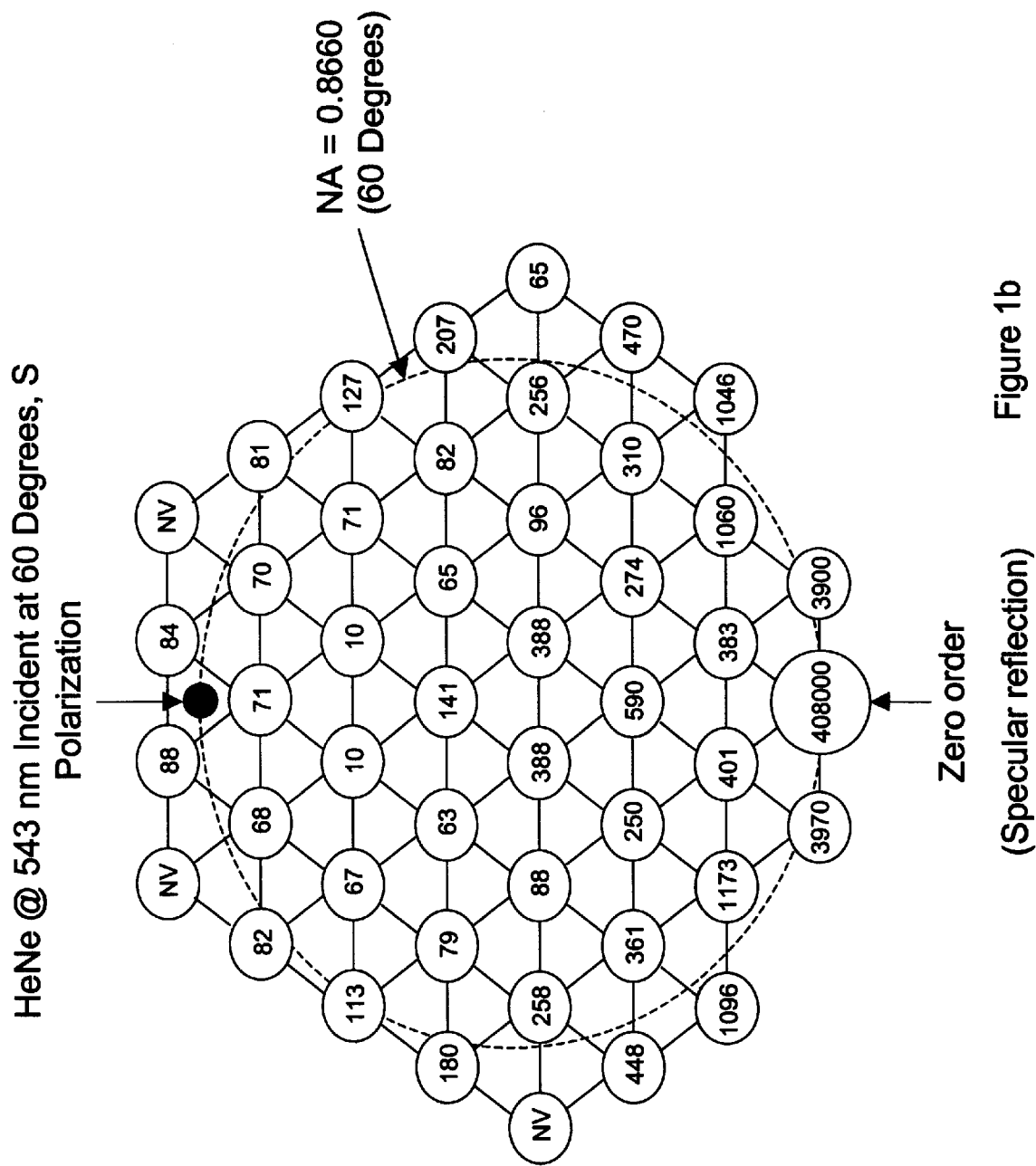
FIG. 1b is a laser diffraction order energy distribution taken under the same conditions used to generate the distribution of FIG. 1a, but for clogged vias.

The effects of via errors on the re-distribution of scattered and diffracted energy can be seen from experimental measurements in FIGS. 1a and 1b. FIG. 1a shows measurements of diffracted components from a die containing good vias with a 0.35-micron diameter and FIG. 1b shows measurements from a die containing under etched vias with a 0.35-micron diameter. A 543-nm, s-polarized laser at an incident angle of 60 degrees from the surface normal was used to illuminate the vias. Each diffracted order was then measured using an energy meter. In FIGS. 1a and 1b, each circle represents a measurement of the relative energy level contained in a diffracted order. The re-distribution of the diffracted energy due to the under etch error is shown in FIG. 1b. Note the decrease in energy of the diffracted orders near the incident beam. The magnitude of the re-distribution varies with both the depth of the vias and the slope of via walls. This re-distribution of diffracted energy can be used to detect these errors by doing a comparison between the two far-field diffraction patterns. This significant energy change in the high order diffracted light can be useful for high sensitivity, high speed error inspection. The shapes of the vias that created these far-field diffraction patterns were verified by SEM profile measurements.

Figure 2:
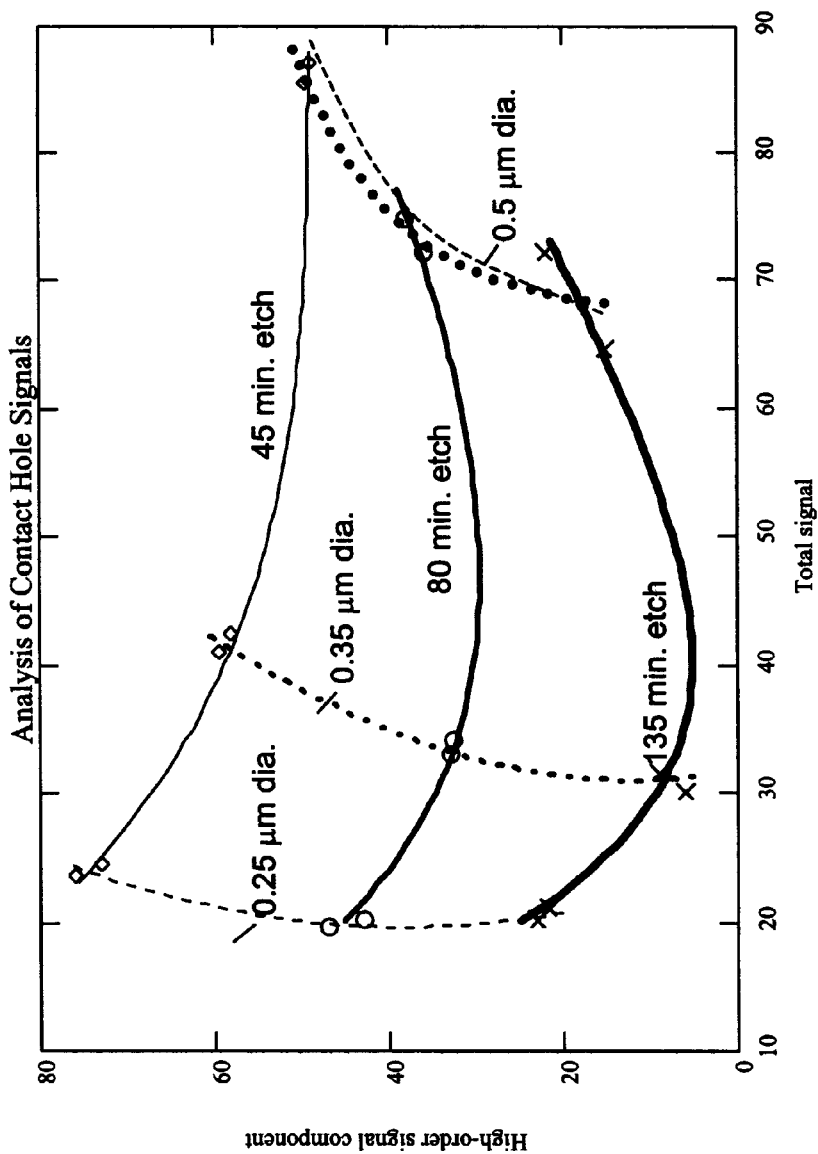
FIG. 2 is a graph showing variations in total collected energy for an entire diffraction pattern and high-order collected energy for the diffraction pattern for similar contact arrays with differing diameter and contact etch times.

The effects of contact hole depth and diameter on the distribution of the far-field pattern can be seen from experimental measurements in FIG. 2. FIG. 2 shows an example graph comparing the total far-field diffraction signal (the x-axis) to the high-order component of the far-field diffraction signal (the y-axis) for contact holes with a known diameter and formed with a known etch time. The total far-field signal represents all the scattered and diffracted light. The high-order component of the diffraction signal represents the intensity of only the higher diffraction orders.

The data presented in FIG. 2 shows that this technique allows for changes in both diameter and etch time of contact holes to be estimated. In this example are nine cases where three contact diameters (0.25 micrometers, 0.35 micrometers, and 0.5 micrometers) are each formed by etching at three different etch times (45 minutes, 80 minutes, and 135 minutes). For the cases shown, increasing the etch time (increasing contact depth) generally corresponds to decreasing the high-order components of the far-field diffraction signal, and increasing the diameter corresponds to an increasing total far-field diffraction signal.

Figure 3:
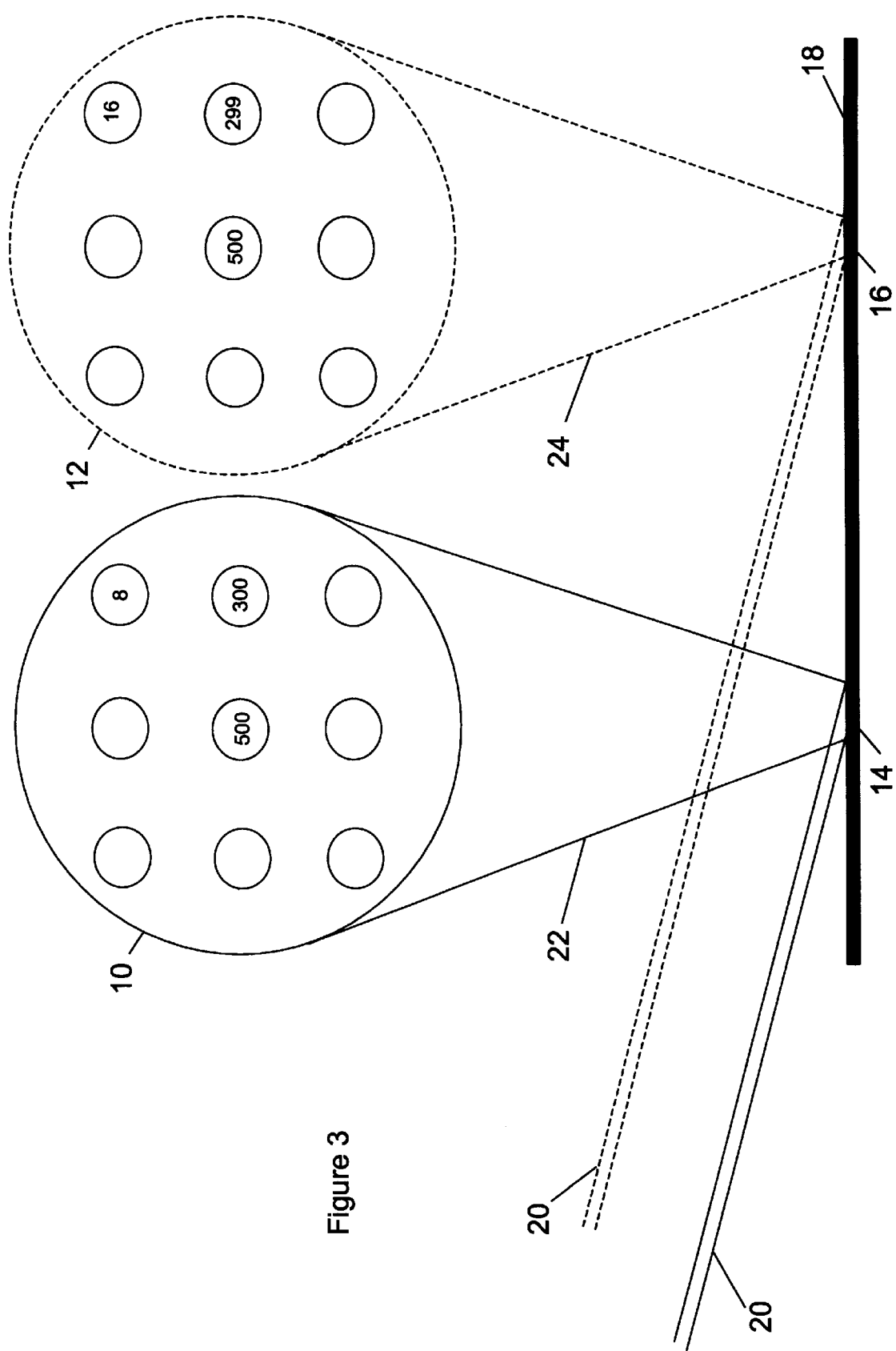
FIG. 3 is a simplified hypothetical illustration of a die-to-die comparison of scattered and diffracted illumination in accordance with an embodiment of this invention.

FIG. 3 illustrates a comparison between two hypothetical far-field patterns of scattered and diffracted light 10 and 12 taken from two regions 14 and 16 on a given wafer 18. Light from incident beam 20 strikes regions 14 and 16 (typically at different times) which is scattered and diffracted by the surface features of these regions to produce scattered and diffracted radiation 22 and 24. Far-field patterns 10 and 12 are recorded at or near the Fourier plane of the illuminated regions. For this invention, the term Fourier plane refers to the optical Fourier plane which is well known to anyone skilled in optics. These locations ideally would have identical surface topologies, but through non-uniform processing, reticle errors, or other fabrication problems have some slight differences in topology. For example, their surfaces may contain a collection of vias, some of which have slightly different etch depths, etch diameters, or etch angles in two different die.

Far-field patterns 10 and 12 are two dimensional distributions of the light intensity. Bright regions are illustrated as circles in FIG. 3. The spatial distribution and intensity of the bright regions varies depending upon such features as the wavelength of the incident beam, the angles of the incident beam and the imaged region of the Fourier plane with respect to the wafer surface, and the surface features on die 14 and 16. Given the same measurement conditions, then variations in such topology from region-to-region will be reflected as variations in the diffraction patterns 10 and 12.

The hypothetical far-field patterns illustrated in FIG. 3, consist of nine diffraction orders. In these far-field patterns, each corresponding order has the same spatial location and only small changes in intensity except for the top-right order. The center orders each have an intensity of 500 microwatts, the right middle orders each have an intensity of 299–300 microwatts, etc. However, the top right order in pattern 10 has an intensity of 8 microwatts and the top right order in pattern 12 has an intensity of 16 microwatts. This represents a physical difference between the illuminated regions 14 and 16. That difference might be, for example, the presence of a residue in certain vias in region 16 but not in region 14. Or it might be a difference in etch profile for one or more of the vias in the illuminated regions.

The significance of the deviation in the top-right order depends on the physical surface feature(s) that it corresponds to and the tolerance of the measurement. Possibly, it corresponds to a small difference in etch depth. This difference in etch depth may be well within the tolerance allowed for the semiconductor fabrication process employed. The deviation may indicate some process equipment is beginning to operate improperly, but at the moment the problem is not serious. Alternatively, the deviation might correspond to a large error in the etch angle. This could give the manufacturer sufficient cause for concern that it discontinues processing, at least temporarily, to carefully evaluate its process equipment.

Figure 4:
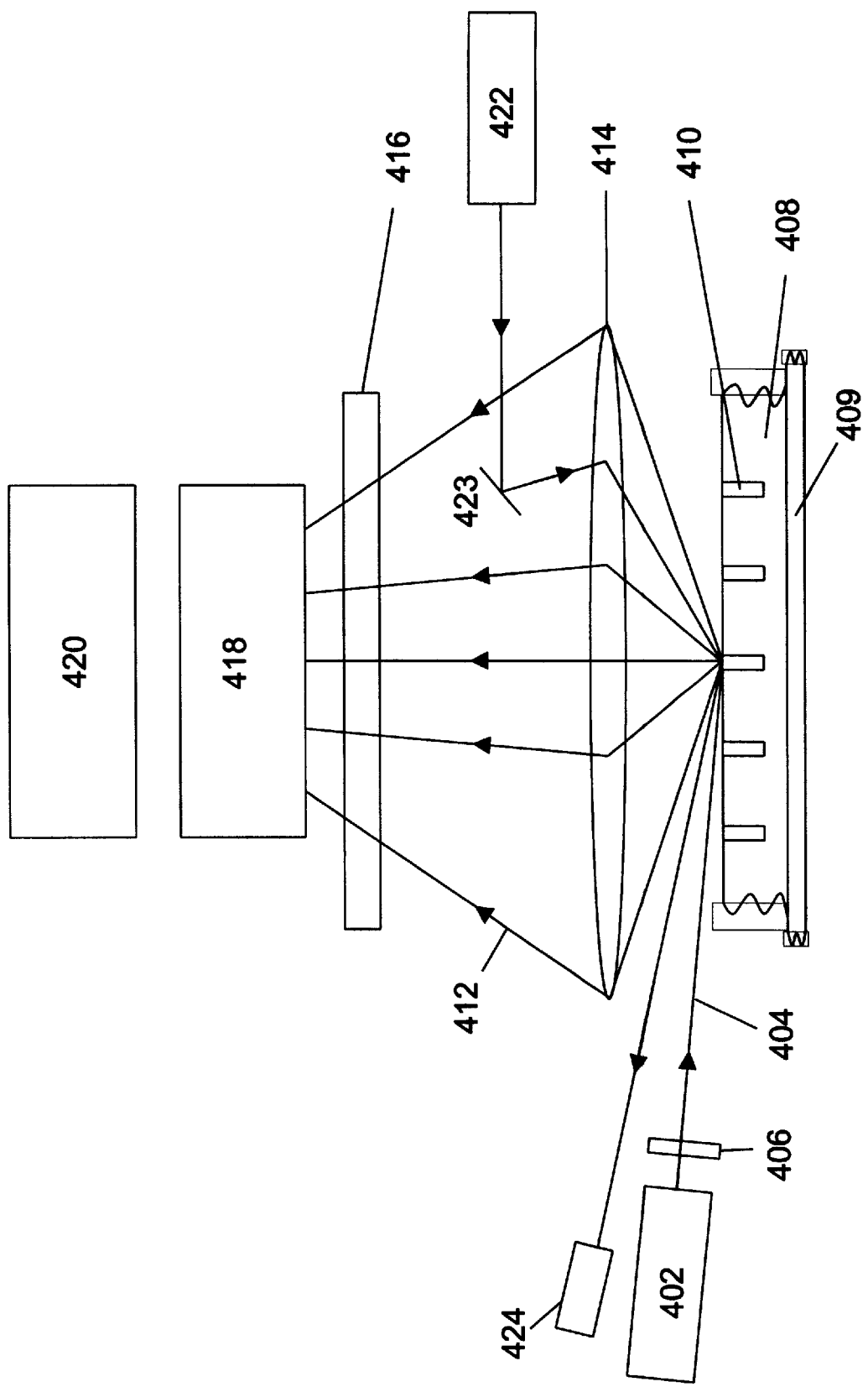
FIG. 4 is a schematic illustration of various components in an apparatus for detecting and comparing diffraction signals in accordance with one embodiment of this invention.

FIG. 4 is a schematic of a relatively simple apparatus for implementing the present invention. As shown, a light source 402 emits a light beam 404 which may be polarized, collimated, or otherwise shaped by optics 406. Light beam 404 is incident upon a layer 408 having a plurality of topological features. In this example, these features are a plurality of vias or contact holes 410. When light beam 404 strikes the surface of layer 408, it interacts with the vias or contact holes 410 and is scattered and diffracted over a wide area above layer 408. The scattered and diffracted light 412 is captured and focused by a lens system 414. Scattered and diffracted light 412 is then directed to optional analyzing optics 416 which can improve the sensitivity of the apparatus. Examples of elements in analyzing optics 416 include apertures for selecting portions of the far-field pattern, Fourier filters, and polarizers. Multiple optical systems comprising 414 and 416 may be implemented in one apparatus to facilitate high speed inspection.

A pattern of scattered and diffracted light 412 at or near the Fourier plane is captured by a sensor 418 which may be a camera or other radiation sensor. Multiple sensors 418 may be implemented in one apparatus to facilitate high speed inspection. The far-field diffraction pattern captured by sensor 418 is provided to a computer 420 which can conduct the appropriate analysis, such as comparisons with other known far-field patterns or other far-field information to determine whether there is a problem with the surface of layer 408. Computer 420 may also include logic for classifying errors on the surface of layer 408 as evidenced by variations between the current far-field pattern and other known far-field patterns.

In general, the system performance can be optimized by adjusting the illumination wavelength, polarization, incident angle, and adjusting the analyzing optics. The angle of illumination is often chosen close to grazing incidence in order to produce high order scattered and diffracted components. These high order components frequently have the highest sensitivity to process variations. The high order scattered and diffracted signals can be collected by properly positioning the sensor 418. When a coherent source is used for illumination, the resulting far-field pattern of scattered and diffracted light is typically referred to as speckle. The speckle pattern is very sensitive to the structure of surface layer 408. Thus it can accurately measure process variations such as under etched vias and residue in the bottom of deep trenches.

Light source 402 may be any source of radiation having good coherence. Examples of preferred light sources are lasers such as ion lasers, Helium Neon lasers, excimer lasers, tunable wavelength lasers, multiple wavelength lasers, diode lasers, etc. Tunable wavelength lasers or multiple wavelength lasers offer the advantage that different wavelengths are selectable to optimize the system performance. Other sources might include a LED or high intensity lamp with a narrow band pass filter. Possible lamps include Hg-Xe lamps, Xe lamps, Excimer lamps, $D_2$ lamps, halogen lams, etc.

A light source should be chosen with a wavelength appropriate for the features to be evaluated. Generally, smaller features (or features separated by shorter distances) require shorter wavelength illumination. Shorter wavelengths give diffraction signals with smaller angles between diffraction orders, thereby allowing more of the scattered and diffracted orders to be captured by the system optics. For example, consider small features with a spacing of 0.5 $\mu$m which are illuminated by light at a 30 degree angle to the surface normal. If the light has a 0.5 $\mu$m wavelength the angle between the zero and first diffracting orders is 60 degrees, where as if the light has a wavelength of 0.25 $\mu$m the angle between the zero and first diffracting orders is 30 degrees.

The light source may include a scanner allowing it to scan surface features. The scanner could move an illuminating spot or line across the region of interest. One embodiment of this type of system employs a line scanner for high speed inspection. A bright line light source can be used for this purpose. The light source can illuminate a line on the region of interest with a length from one micron to the full diameter of a semiconductor wafer. Typically, longer illumination lines have the capability for faster inspection speeds with reduced defect localization compared to shorter lines. The line should be significantly wide as to cover several repeating features. This will increase the stability of the far-field pattern as the illumination line is scanned across the region of interest. As the line is scanned, the far-field pattern is monitored. If the patterns in the region of interest are repeating, such as memory areas on a semiconductor wafer, then the far-field pattern should not change as the illumination line is scanned across the region. Changes to the far-field pattern as the wafer is scanned may indicate errors in the surface features.

As shown in FIG. 4, a light source 422 may also illuminate the surface through the capturing optics using an auxiliary mirror or beam splitter 423. This light source can be the same type as 402 or it can be a different type such as those described above. Light source 402 can also be redirected and used as light source 422. Using a light source that illuminates through the capturing optics has the advantage that it is easy to change the illumination angle, simply by changing the position of the beam through the capturing optics. In this way, illumination at angles from normal up to the maximum capturing angle of the optics is possible. This illumination technique has the disadvantage that multiple reflections from the surfaces of the lenses can reach the sensor 418 and reduce the signal-to-noise ratio. To reduce this effect, high quality anti-reflection coatings are required. In addition, the specular reflection from the surface (zero order diffraction) can return through the capturing optics. This specular reflection is generally much greater than the other scattered and diffracted orders and may need to be blocked or attenuated to prevent saturation of the sensor or to improve the signal-to-noise ratio of the measurement.

Polarizing optics 406 may be used to impart a desired polarization to incident beam 404. This can enhance the signal to noise ratio of the errors of interest. For example, the via errors in FIGS. 1a and 1b show a greater signal-to-noise ratio when using S-polarized light, compared to P-polarized light. Capturing optics 414 should capture scattered and diffracted radiation over a sufficiently large angular range to record radiation from many different diffraction orders. Because the features being evaluated are quite small, the far-field region begins rather close to the substrate. Generally, the capturing optics may include one or more lenses (including holographic or diffractive surfaces) and possibly a screen such as a ground glass element on which the diffraction pattern appears. The screen could be a diffuse surface or volume scatterer, a fluorescent surface, or a phosphorescent surface. If a screen is employed, additional optics may be required to transfer this image to sensor 418.

In a preferred embodiment, wafer 408 is mounted on an X-Y translation stage 409 which moves the wafer surface relative to the incident light beam 404, without affecting the relative positions of collection optics 414 and light source 402. In a die-to-die comparison, the diffraction signals of a first die associated with a first position of X-Y stage 409 are stored in computer 420 and then compared with the diffraction signals of a second die associated with a second position of X-Y stage 409. Misalignment of the dies only changes the phase in scattered and diffracted signal, not the intensity. Thus, doing comparisons in the Fourier domain has the additional benefit of being insensitive to alignment errors between the two different positions. This allows the use of a less expensive, lower precision stage. The stage can also be used in a scanning mode similar to the concept described previously on scanning illumination. For example, repeating features on a wafer can be illuminated by a line. The stage can then move in a direction perpendicular to the line. If there are no changes in the repeating features, the far-field pattern will not change. Sensor 418 should be able to record the diffraction pattern at the Fourier plane with a high resolution. Preferably, it will output the diffraction pattern as electronic signals which has been predigitized or may be easily digitized by an analog-to-digital converter. Examples of suitable sensors include CCD arrays, CMOS photodiode arrays, photogate arrays, TDI arrays, etc. In some cases, one or more single channel sensors may be employed. An example of this is when a system is optimized to monitor a particular type of error.

As shown in FIG. 4, an optional auxiliary sensor or sensors 424 may also be used to capture scattered and diffracted light that is missed by the capturing optics 414. In some situations it may not be possible or practical to have capturing optics 414 that collect the highest angle diffraction. This could be a potential problem if some of the high angle scattering and diffraction contains information about the errors of interest. In this case, auxiliary sensors 424 can be positioned to capture the scattering and diffraction that escapes the collecting optics 414.

Computer 420 may be any suitable system having an appropriate CPU and memory for storing far-field data and program instructions for implementing the necessary comparisons of the two or more diffraction patterns. Examples include workstations, personal computers, embedded systems, etc.

Figure 5:
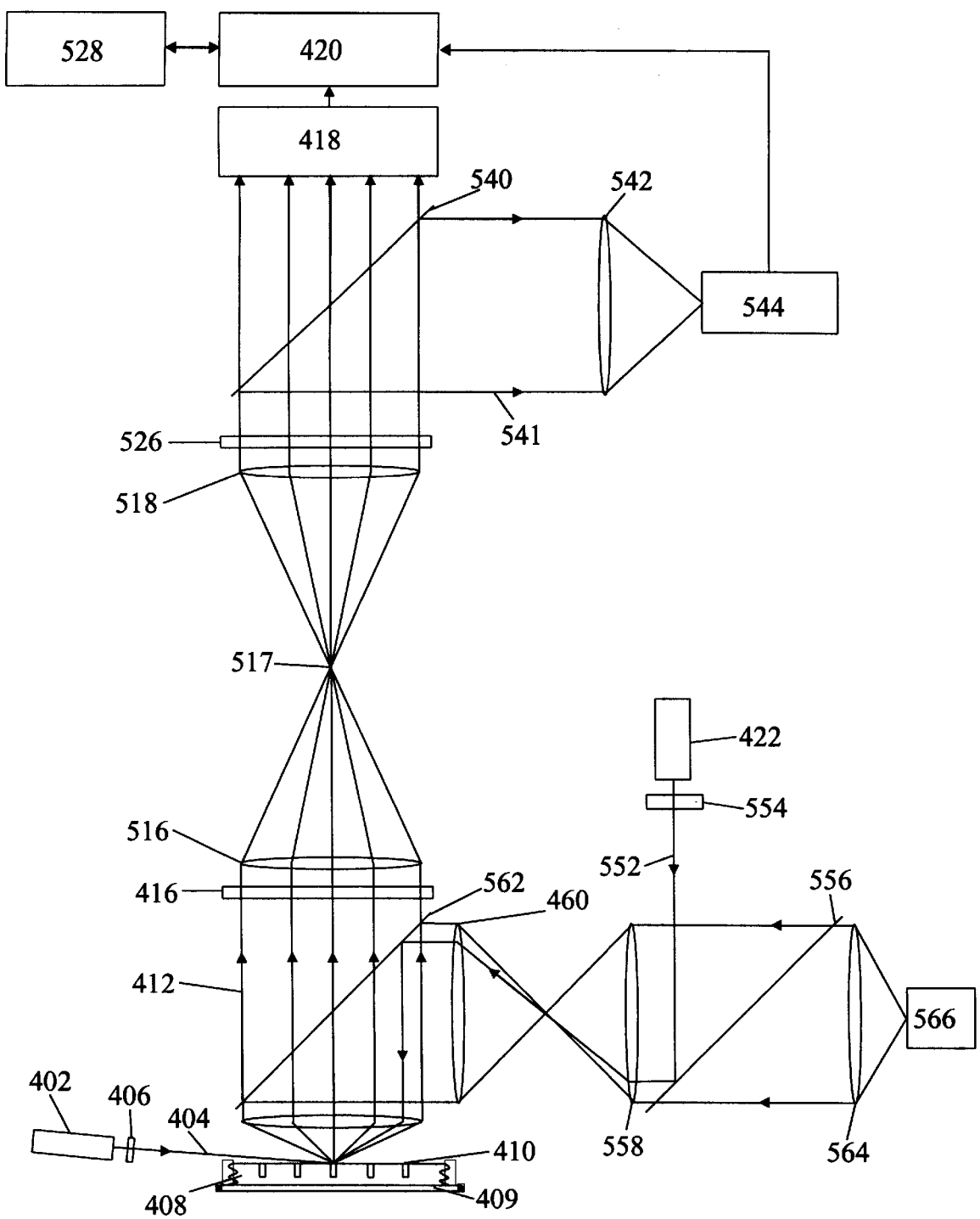
FIG. 5 is a schematic illustration of various components in an apparatus for detecting and comparing diffraction signals in accordance with another embodiment of this invention.

FIG. 5 is another schematic of an apparatus for implementing the present invention. This apparatus includes many of the same features as the FIG. 4 apparatus. In the two figures, like reference numbers refer to like features. Thus, light 404 from a light source 402 diffracts when it illuminates the surface of layer 408. Light 552 from light source 422 may also be used to illuminate the region of the layer. Scattered and diffracted light 412 is provided to analyzing optics 416 and ultimately to sensor 418. In addition, between analyzing optics 416 and sensor 418 the apparatus includes lenses 516 and 518. These lenses are used to provide a field plane that can be used to limit the area of interest on the wafer and an additional Fourier plane for analyzing optics 526. The analyzing optics at 416 and 526 could be an aperture or Fourier filter that blocks or attenuates scattered and diffracted far-field light to improve the signal-to-noise ratio. The operation of an aperture can be better understood by referring back to FIG. 3. For example, an aperture may be employed to increase the signal to noise ratio of the signal provided in the top-right spot in the diffraction patterns 10 and 12. Specifically, aperture 526 in FIG. 5 may be inserted in or near the Fourier plane and in front of the detector. This aperture will block or attenuate the high intensity far-field light which may not be relevant to the evaluation of interest (assuming that the top-right order is the only order containing the information of relevance). For example, the aperture may block the center and middle-right orders in diffraction patterns 10 and 12. The aperture may also be used to block the so called zero order specular reflection from the surface being illuminated.

Generally, the Fourier filters employed in this invention will be made to block diffraction orders from repeating surface features known to be of little relevance to an application at hand. The filters will include opaque regions of the approximate sizes, shapes, and locations of the diffraction orders to be filtered. The remainder of the filter is transparent, thereby allowing diffraction orders of interest to be recorded by the detector. Another type of Fourier filter selectively attenuates bright regions so that the far-field pattern can be easily measured by one sensor. This approach has the advantage that no information is lost form the far-field pattern. The extra information collected from the attenuated regions can allow for improved measurements and comparisons. Suitable Fourier filter designs are known in the art and are described in U.S. patent application Ser. No. 09/070,437 filed on Apr. 30, 1998, naming Eliezer Rosengaus and Steven R. Lange as inventors, and titled A SYSTEM AND METHOD FOR INSPECTING SEMICONDUCTOR WAFERS. That application is incorporated herein by reference for all purposes.

The apparatus of FIG. 5 also includes an optional memory or database 528 of stored baseline information coupled to computer 420. These baseline information may be obtained empirically or by simulation. In one specific embodiment, the baseline information is actual data for surface features that have a known error (e.g., over etched vias). This particular error may have been identified in the past when the process equipment was known to be malfunctioning.

The apparatus of FIG. 5 also includes a subsystem for generating a spatial image of the wafer from the scattered and diffracted light. This subsystem includes a beam splitter 540 which splits scattered and diffracted light beam 412 at a location downstream from lens 518. Beam splitter 540 splits beam 412 into a reduced intensity continuation of beam 412 and a separated beam 541. A lens 542 focuses light beam 541 onto a sensor 544 which may be a camera or other sufficiently high resolution detector which can record a spatial image of layer 408. This spatial image may be used to align layer 408 and review the effect of the Fourier filter or aperture 526 on the image, for example.

The apparatus of FIG. 5 also includes a light microscope subsystem which allows the user to perform optical microscopy on layer 408. Thus, microscopic inspection of the substrate can be conducted in parallel with the diffraction method of this invention. In the light microscope subsystem, a light source provides light to a layer 408 via various optics. This light source 566 could be any of those mentioned earlier for light source 402. In one preferred embodiment, this light has a bandwidth greater than 50 nm to minimize interference effects, such as the light produced by a Halogen lamp. In another embodiment the light source is the same as light source 402 or 422. The light then reflects, scatters, and diffracts off the wafer through the capturing optics to a mirror or beam splitter 540. The beam splitter or mirror 540 directs the beam through lens 542 which produces a light microscope image of the wafer on sensor 418.

Figure 6:
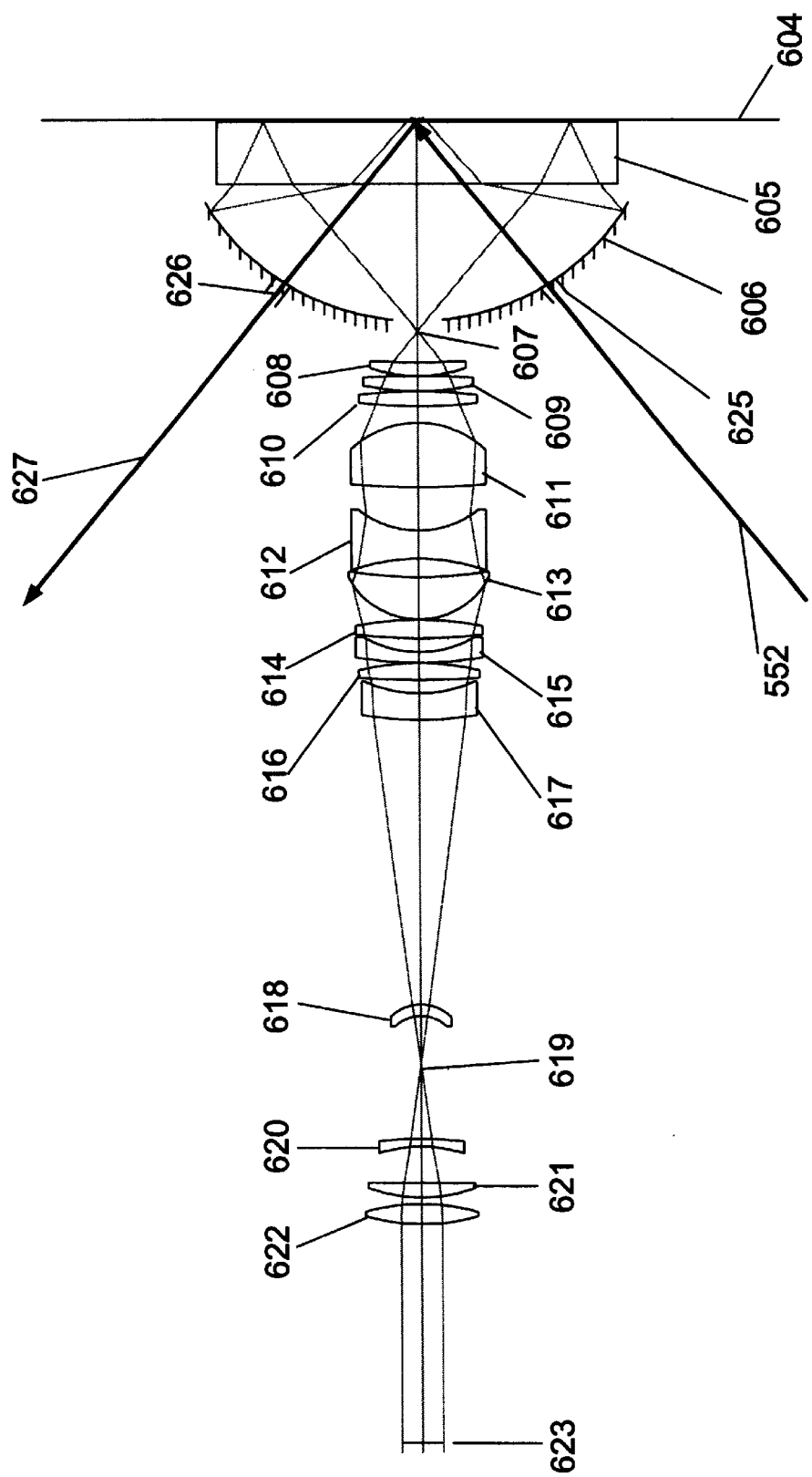
FIG. 6 is an embodiment of an optical system that can support illumination of the substrate surface and capturing the scattered and diffracted light at angles up to 79 degrees.

FIG. 6 shows one embodiment of an optical system that can support the apparatus previously described. This optical system is described in U.S. patent application Ser. No. 09/046,814 filed on Mar. 24, 1998 naming Yung-Ho Chuang, et. al. as inventors, and titled HIGH NA SYSTEM FOR MULTIPLE MODE IMAGING. That application is incorporated herein by reference for all purposes. The design uses all fused silica glass with a 0.98 NA, 2.0 mm field size, a 7.653 mm focal length, and 0.75 millimeter working distance. It is optimized for use at a wavelength of 0.266 micrometers where the index of fused silica is 1.499776.

This embodiment of the optical system allows simultaneous illumination of the substrate surface and capturing the scattered and diffracted light at angles from near normal up to 79 degrees. This is due to the high numerical aperture (NA) of the design and the unique illumination through the dome shaped spherical reflector. Other designs are disclosed in the above reference that extend the angular range up to 85 degrees. The light 552 first passes through an aperture 625 in the dome shaped reflector 606. The light 552 then passes through both surfaces of element 605 and illuminates the surface 604. The specular reflection 627 (zero order) then passes through element 605 again and through another aperture 626 in the dome shaped spherical mirror and escapes from the system. These apertures in the dome shaped reflector 606 may be in the form of stripes in the reflective coating on the spherical reflector 606 allowing many different illumination angles to be easily chosen. Unique illumination through the dome shaped reflector 606 is a significant advantage in this design. The illumination 552 only passes through two surfaces, limiting the possibility of reduced signal-to-noise from multiple reflections.

Figure 7:
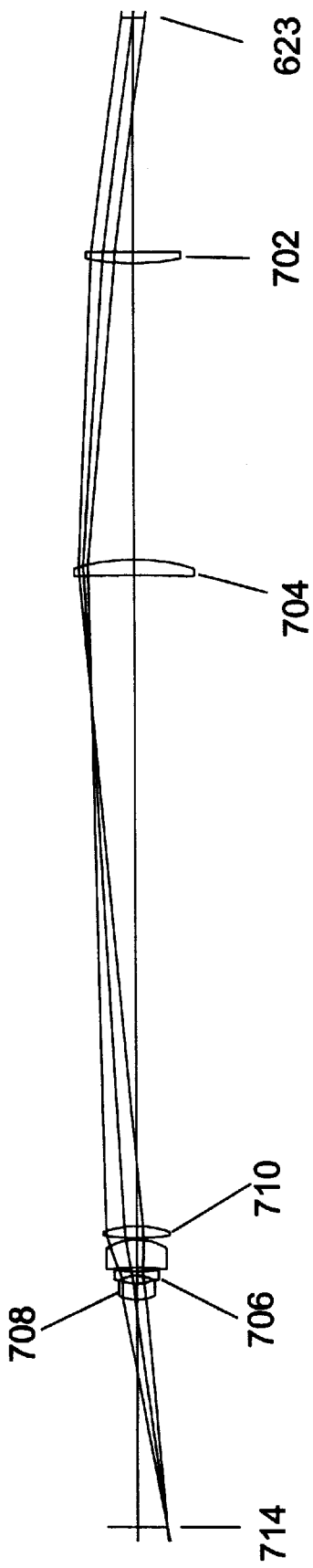
FIG. 7 is an embodiment of an optical system that can collect the far-field light and form an image of the surface features.

The optical design uses a series of lenses and mirrors 605–622 to provide an external pupil plane 623 conjugate to the internal pupil plane of the objective as shown in FIG. 5. This pupil plane 623 will exactly correspond to the Fourier plane of the sample surface 604 because it is also in the collimated range of the objective. This external pupil plane 623 allows for improved access to the Fourier plane for Fourier filtering and aperturing. An additional varifocal tube lens shown in FIG. 7 can be used to produce an optical image of surface 604. This tube lens uses a series of lenses 702–712 to collect light from the Fourier plane 623 of the lens system in FIG. 6 and form an optical image of surface 604 at image plane 714. This imaging can be done in combination with the Fourier filtering and aperturing to increase the signal-to-noise for the defect types of interest. This makes these optical systems ideally suited for the apparatus described in FIGS. 4 and 5.

Figure 8:
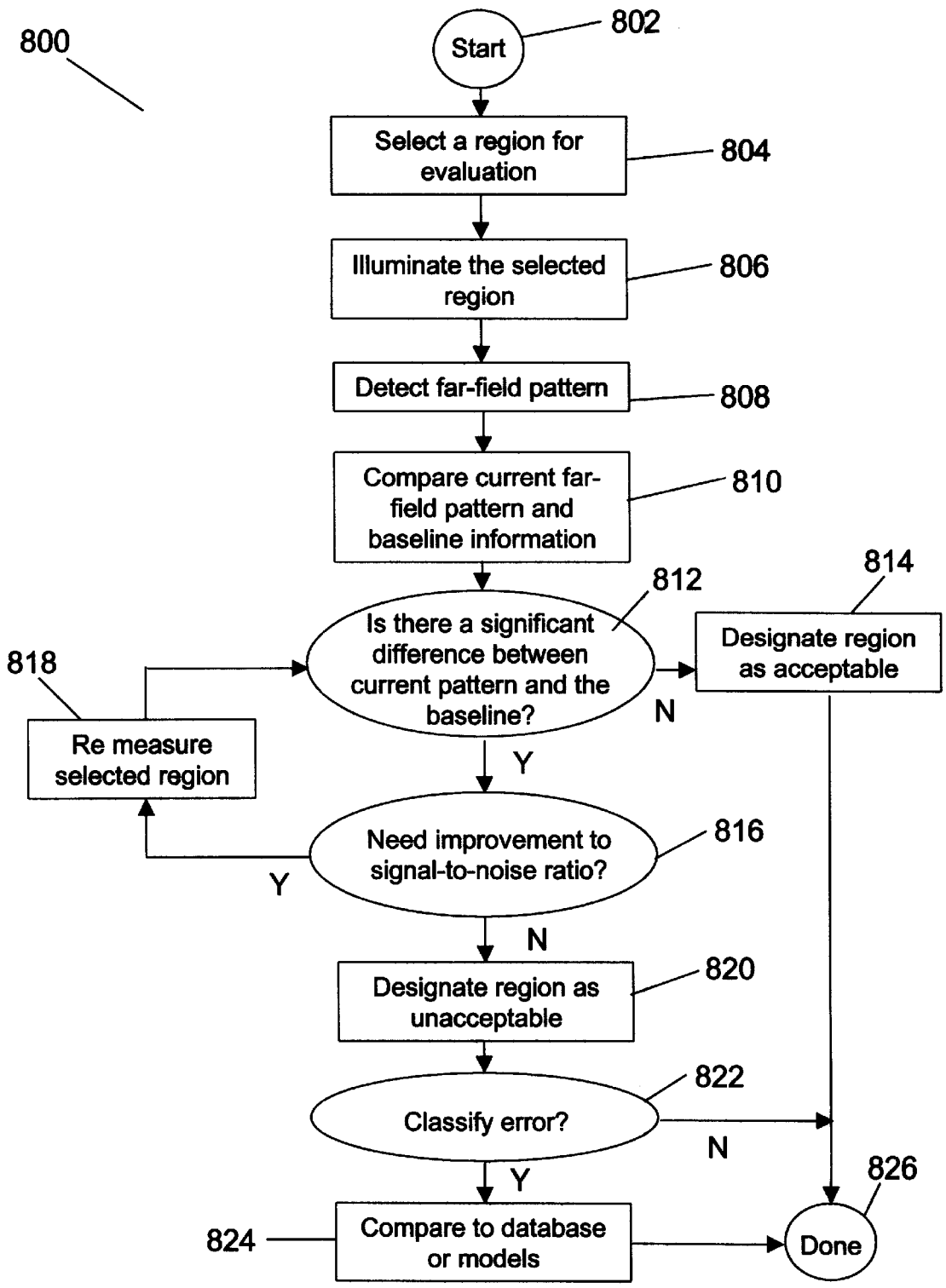
FIG. 8 is a high level process flow diagram of a method that may be used to implement the present invention.

This invention may be implemented as a series of method steps. One method of implementing the invention is depicted in FIG. 8. As shown there, a method 800 begins at a point 802 and in a step 804, the system identifies a region on the substrate for evaluation. This region may be a die or zone on a semiconductor substrate, a portion of a reticle, etc. In the case of die-to-die comparison, it may simply be a region in the next successive die in a series of dies to be evaluated on a wafer.

Next, at a step 806, the system illuminates the region selected in step 804 with radiation from source 402 or 422. The topological variations on the selected region cause some of the incident light to diffract. The scattered and diffracted light is then detected in the far field (see step 808) via detector 418 for example. At this point, the system can compare the far-field pattern of the selected region with baseline information (see step 810). The baseline information can come from various sources. For example, it could be a simulated pattern of scattered and diffracted light. It could also be a previously recorded far-field pattern taken from similar surface features or it could be a far-field pattern of another zone or die taken from the same substrate. These baseline diffraction patterns can be stored in a baseline database 528 or temporarily stored in memory. In order to improve the speed of the operation, the steps in FIG. 8 may be performed partially or fully in parallel.

Comparison step 810 may be performed with the aid of computer 420. It identifies any potentially relevant differences between the current and baseline diffraction patterns. Differences in location and intensity of far-field patterns are noted. Next, the system determines whether any differences are in fact relevant at a step 812; i.e., are there significant changes between the baseline information and current far-field pattern? If not, the system denotes the surface region as acceptable at a step 814.

At this point, the process could conclude. However, it is possible that observed differences in the baseline information and current far-field pattern are due to noise. Therefore, in some embodiments, it may be desirable to take further images in which the signal to noise ratio is improved. Thus, should the system determine that there are significant differences between the baseline information and current far-field patterns (step 812 is answered in the affirmative), then the system may next determine whether the detection portion of the system should be modified to improve signal to noise ratio (step 816). If so, the system re-images the selected region at a step 818. Various techniques may be employed to improve the signal-to-noise ratio. One such technique is the insertion of an aperture, Fourier filter, or other analyzing optic (as described above) at or near the Fourier plane. This can remove or minimize the diffraction signals that contain information unrelated to the sought after details. It may also be necessary to regenerate the baseline information. In die-to-die comparisons of far-field patterns, for example, this might involve re-measure the original baseline region as well as the current region under inspection. If the originally detected differences between the current far-field patterns and the baseline far-field pattern are within the allowable tolerances, the substrate region is designated as acceptable (step 814) and the method concludes at 826.

Of course, the originally detected differences between the current far-field pattern and the baseline information may be so great as to be unambiguous. In such cases, step 816 is answered in the negative and the system designates the selected region as unacceptable (step 820). In the context of quality control, an unacceptable designation may indicate to the manufacturer that the current substrate should not be processed further. In the context of process monitoring, such designation may indicate that the process equipment or conditions are failing, at least temporarily. After the substrate region is designated as unacceptable (step 820) the system can then determine if error classification is required (step 822). If error classification is not required, the method concludes at 826. If error classification is required then a comparison can be made between the current diffraction pattern and other known baseline diffraction patterns stored in memory or a database (step 824). Algorithms can also be implemented to search for signatures which are characteristic of common defects such as scratches and additional information on defects such as orientation can be recovered. After error classification, the method concludes at 826.

Figure 9:
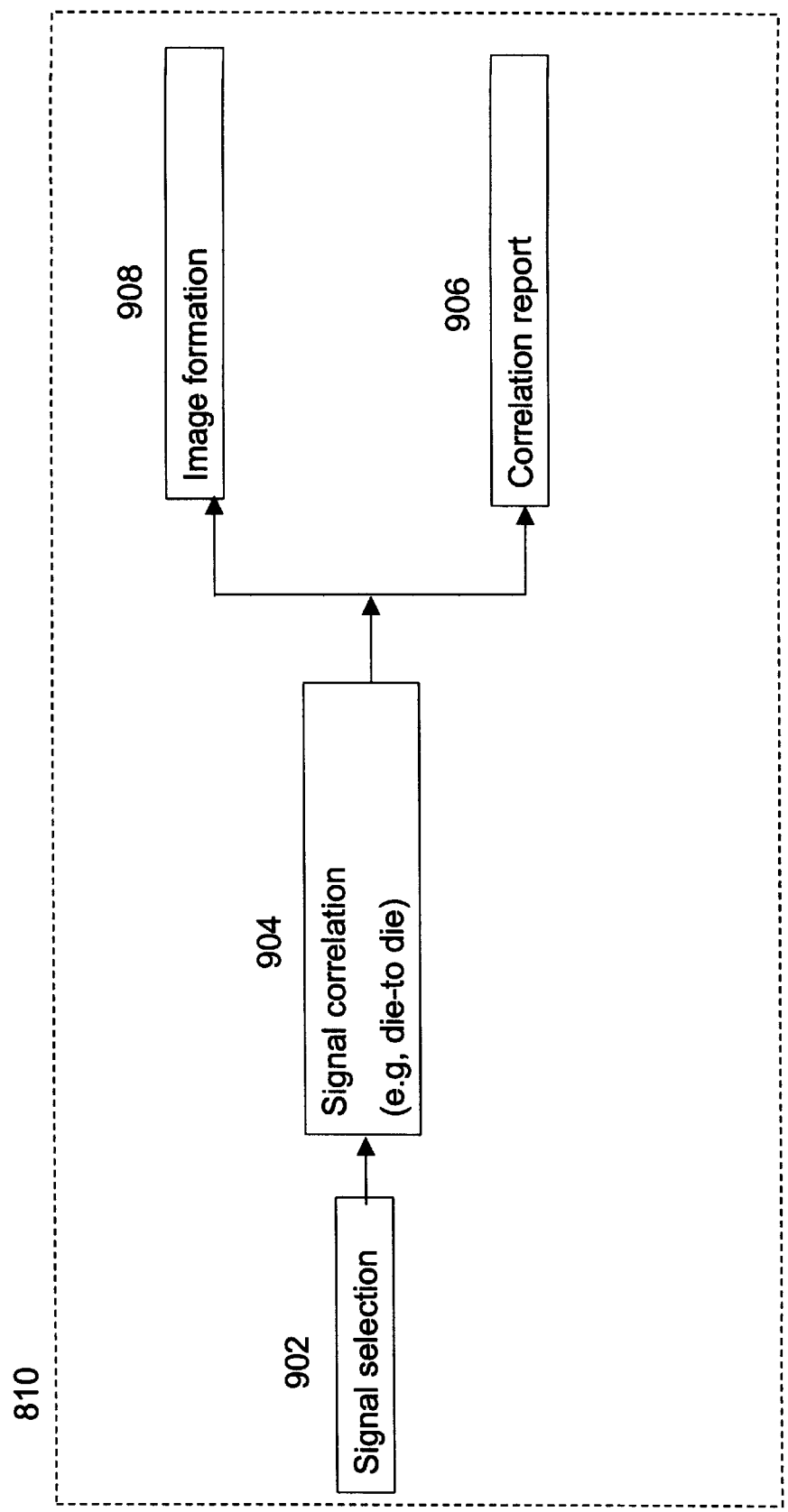
FIG. 9 is a process flow diagram of a method for comparing a baseline diffraction pattern with a recently acquired diffraction pattern in accordance with an embodiment of the present invention.

FIG. 9 shows a general image processing flow suitable for some embodiments of this invention. This flow may correspond to step 810 of FIG. 8. First, at a step 902, the baseline diffraction pattern is selected. Second, correlation between the current far-field pattern and the baseline information is performed at a step 904. This may include least squares fitting and cross-correlation analysis of the diffraction spots in the diffraction signals. After analysis is completed, the result can provide real time error statistics (output 906) for in-line inspection or generate an image (output 908) for off-line review.

The baseline information that is selected (step 902) may take several different forms. In one instance, it is information from an adjacent pattern or cell on the same die. This is a cell-to-cell comparison in which similar regions of the same die are illuminated and compared. In another instance, it is information from a die on a semiconductor wafer, similar to the die currently being evaluated. This is a die-to-die comparison in which the same region of multiple dies are illuminated and compared. In yet another instance, it is information from a die on a different semiconductor wafer, similar to the die currently being evaluated. This is a wafer-to-wafer comparison in which the same region of a die on different wafers are illuminated and compared.

The baseline information can be a stored far-field pattern for a similar surface having known characteristics (e.g., via depth, diameter, and tilt), or it is from a known good surface. The stored baseline far-field pattern may have been generated earlier from a sample having such known characteristics. Alternatively, the baseline far-field pattern may be generated by a mathematical simulation of the far-field pattern for a surface having specified features. Principles underlying effective modeling of diffraction patterns from arbitrary surfaces are described by L. Li in "New formulation of the Fourier modal method for crossed surface-relief gratings" Journal of the Optical Society of America A, vol. 14, No. 10, pp. 2758–67 (1997), and in Li, "Modal Method by Fourier expansion for modeling crossed gratings," SPIE proceedings, vol. 3010, pp. 18–29 (1997), both of which are incorporated herein by reference for all purposes.

The type of baseline information selected may depend on the information the comparison will provide. For example, in the semiconductor industry problems with a reticle will typically be limited to specific features on one of multiple dies on the reticle. Thus, a die-to-die comparison may be most appropriate for reticle evaluation. In the case of a process problem such as an over aggressive etch, all die may suffer from the same problem (e.g., vias cut too deeply into the substrate). When this occurs, a die-to-die comparison may not be appropriate, as it would only show a discrepancy between the different dies on the same wafer (all die would suffer from the same problem). In this case, the baseline might be a far-field pattern for a die known to have vias of the proper depth, diameter, and tilt. Alternatively, the same section of a wafer or die can be monitored from wafer-to-wafer to get trend data and statistics useful for diagnosing future process excursions.

Figure 10A:
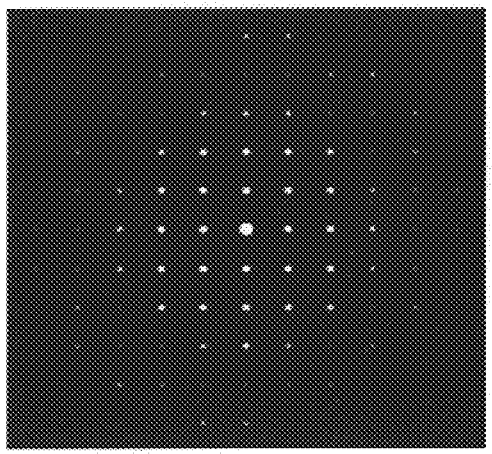
FIG. 10a is a computer simulation of a far-field pattern produced by good vias.
Figure 10B:
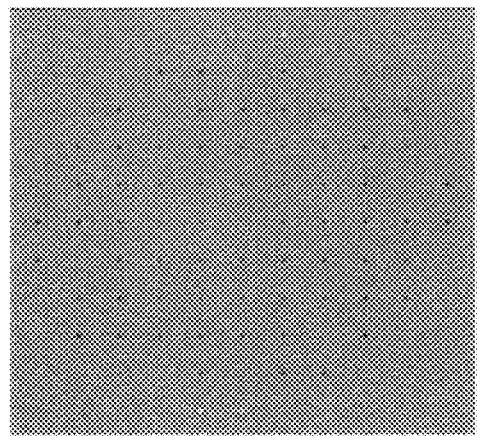
FIG. 10b shows the sensitivity of the diffracted orders in FIG. 10a to a particular process error.

To obtain the greatest signal-to-noise when doing a correlation between the current diffraction pattern and the baseline diffraction it is often necessary to identify the regions of the far-field patterns that contain desirable information. To facilitate identification of those diffraction orders one may employ a detailed mathematical model of the scattering and diffraction physics to predict the location of such orders. Suitable modeling techniques are described in the Li articles mentioned above. Once these orders are identified, they can be used to optimize the computer correlation or modify the apparatus to improve the signal-to-noise from the measured diffraction patterns. An example of this type of computer simulation is shown in FIGS. 10a and 10b. FIG. 10a is a simulation of the expected far-field pattern produced by an array of vias. A simulation of a particular process error can then be made and the resulting far-field pattern compared to that in FIG. 10a. FIG. 10b shows the relative change in each of the orders due to the process error. The more the process variation effects a particular order, the darker or brighter the order will appear compared to the background gray level. FIG. 10b shows the orders farther from the specular reflection are more sensitive to the process variation.

Once the orders that contain desirable information are identified, they can be used to improve the computer correlation. For example, with repeating via arrays, a correlation of the diffraction orders among dies may be performed to identify surface locations with errors. With non-repeating via distributions, Fourier plane zone to zone correlation among dies may be performed.

Also, after the orders that contain desirable information are identified, modifications to the apparatus that enhance the measurement of the diffraction patterns can be considered. For example, a manufacturer concerned about under etching may want to focus on those regions of the far-field containing the most information about via depth. But it may not know how to identify the spots actually containing that information. An accurate mathematical model can provide the identity of such orders for a given apparatus set up and expected via layout. The model could also show how changes in the apparatus set up or via layout will affect the diffraction pattern. Then, the detector orientation, illumination source and angle, and filter configuration (if any) can be chosen to increase the signal-to-noise ratio of those far-field regions containing the information of interest.

Figure 11:
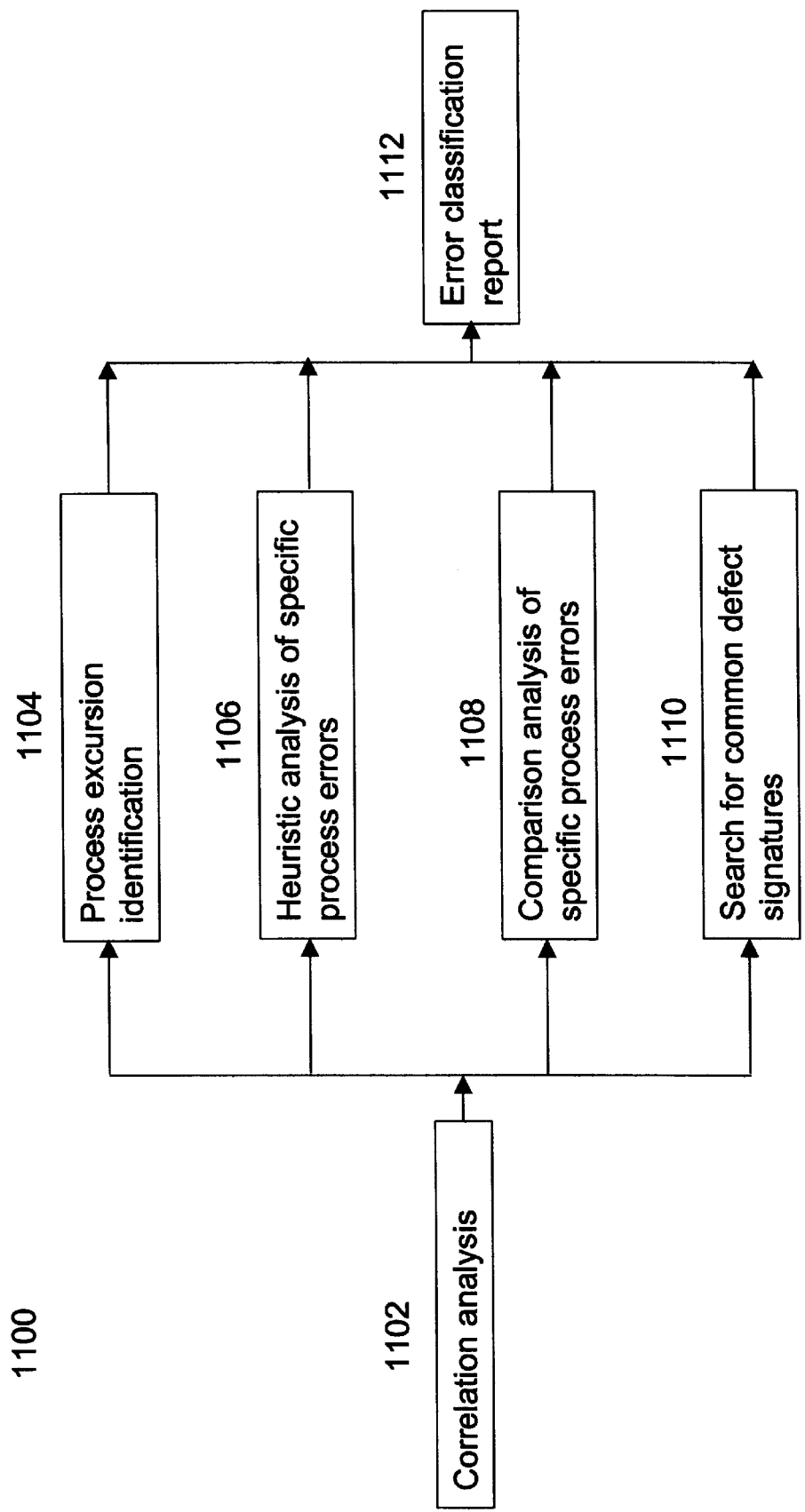
FIG. 11 is a high level process flow diagram of a method that may be used to characterize errors in surface features.

After the current far-field pattern and baseline information have been processed and an error has been detected, it may be of interest to classify the error. FIG. 11 shows a general error classification flow suitable for some embodiments of this invention. This flow may correspond to step 822 of FIG. 8. First, at a step 1102, The method of error classification is chosen. Error classification in this invention may be employed in several ways. Some of these are process excursion identification (step 1104), heuristic analysis of specific process errors (step 1106), comparison analysis of specific process errors (step 1108), and search for common defect signatures (step 1110). After error classification is finished, a error classification report can be generated in step 1112.

One simple approach to classification is to identify when a given die or region of a surface has a diffraction pattern that does not match the expected pattern. This notifies the operator of a potential process excursion without specifying what type of problem it might be (step 1104). Further testing using techniques (e.g., electron microscopy or ion milling) other than those described herein may then be employed to classify the type of error.

In another approach to classification, a system may classify errors by correlating at least some portion of the far-field pattern with particular errors. For example, an increased intensity in a particular cluster of diffraction orders may indicate there are under etched vias. A system suitable for classifying errors according to this technique will contain heuristics for classifying different types of deviations from the baseline information (step 1106). An example of this type of classification is shown in the die-to-die comparison in FIGS. 12a and 12b. FIGS. 12a and 12b show a comparison of high angle diffracted orders for a die with known good vias to dies on wafers with unknown via profiles. FIG. 12a shows that all the dies on this wafer very closely match the known good die, so this wafer is acceptable. FIG. 12b shows the center dies on this wafer do not match the known good die and suffer from under etching.

In an additional approach to classification, a system may classify errors by comparing the far-field pattern of the currently evaluated region against information stored in a baseline database (step 1108). The far-field patterns or data about the sensitivity of different far-field regions stored in the baseline database will be associated with various surface conditions. If the current far-field pattern does not accurately match the expected far-field pattern, then the system may compare the current far-field pattern against each of the other relevant far-field patterns in the baseline database. The one that most closely resembles the current far-field pattern effectively classifies the surface error as being that type associated with the matched pattern. The technique may not find an exact match. Nevertheless, it can indicate a likely form and magnitude of the process excursion. On example of such a classification is to compare the process excursion to the previous process history.

Figure 13:
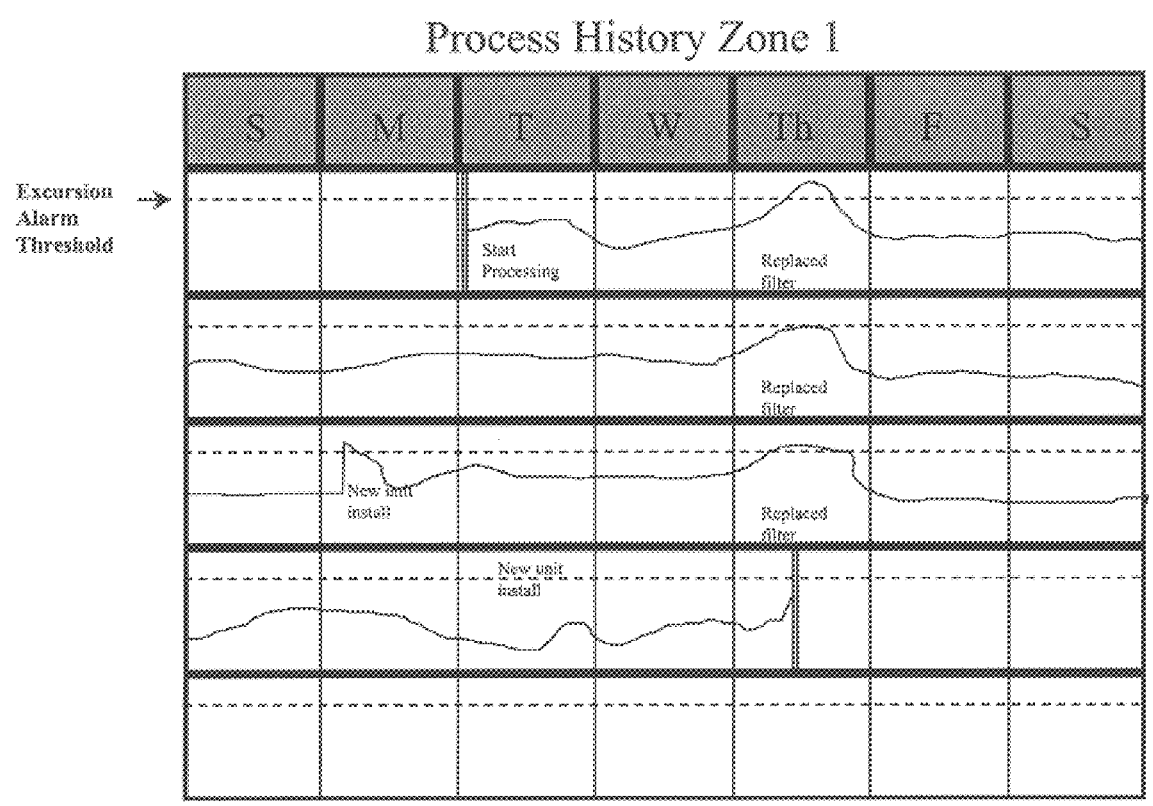
FIG. 13 is a diagram that shows a hypothetical process history that could be used for preventing future process excursions.

Trends in process data can identify process excursions before they become critical and suggest preventive correction. A hypothetical example is shown in FIG. 13. Here a weekly process excursion chart shows that when a filter is due for replacement, an unacceptable process excursion occurs. The solution to this problem may be to replace the filter when the data indicates a similar unacceptable process excursion is about to occur.

The optional memory or baseline database 528 of stored diffraction patterns is coupled to computer 420 as shown in FIG. 5. In the simplest case only a single far-field pattern of a correctly formed surface is stored. By comparing against this pattern, the system can determine whether the surface significantly deviates from the desired structure. In more complicated systems, the baseline database may also contain the far-field patterns of surfaces having variations in one or more parameters. In a preferred embodiment, the database includes the expected far-field patterns for a perfectly formed surface, a surface in which only the opening depth varies from nominal, a surface in which only the opening diameter varies from the nominal, and a surface in which only the opening tilt varies from the nominal. Because most fabrication processes in which problems arise do not initially cause gross deviations in surface topology, the diffraction patterns in the database represent only minor deviations from the nominal surface features. Sometimes the database will also include other far-field patterns to more specifically characterize the deviation from nominal. For example, the database may include one far-field pattern for openings having a greater than nominal diameter and another far-field pattern for openings having a less than nominal diameter. Often, the deviating far-field patterns will have a certain "signature" of variation in intensity from the nominal case. If a surface under consideration contains the same signature in the specified orders, that surface can be classified as having the variation indicated by the database far-field pattern that it best matches.

Other embodiments and advantages will be apparent to those skilled in the art from consideration of the specification and practice of the invention disclosed herein. It is intended that the specification and examples be considered as exemplary only, with a true scope of the invention being indicated by the following claims.

What is claimed is:

1. A method for analyzing the condition of a surface of an electronic device, the surface having a defined pattern, the method comprising:
   (a) illuminating a first region of the surface such that light is scattered and diffracted off of features of the surface;
   (b) detecting light scattered and diffracted from the first region surface;
   (c) comparing the diffracted light detected to a baseline diffraction pattern of light diffracted from a baseline region having a condition corresponding to an expected condition of the first region; and
   (d) determining whether the detected light diffracted from the first region significantly deviates from the baseline diffraction pattern.

2. The method of claim 1, wherein the light diffracted from the first region of the surface forms a far field diffraction pattern that is detected.

3. The method of claim 1, wherein the light diffracted from the first region of the surface forms a far field diffraction pattern of which only a single point of light is imaged.

4. The method of claim 1, wherein the illuminating is performed using a monochromatic coherent light source.

5. The method of claim 4, wherein the monochromatic coherent light source is a laser.

6. The method of claim 1, wherein the surface is a semiconductor wafer surface, the first region is a first die or zone on the semiconductor wafer, and the second region is a second die or zone on the semiconductor wafer.

7. The method of claim 1, wherein the baseline diffraction pattern is diffraction data taken from a surface having the expected condition of the first region.

8. The method of claim 1, further comprising selecting the baseline image from a database of images, the database of images comprising diffraction patterns of regions which vary from a nominal image for the first region.

9. The method of claim 1, further comprising:
   filtering or polarizing far field light before detecting light diffracted from the first region of the surface.

10. A method for inspecting a plurality of openings in a film on a substrate, comprising:
    illuminating a first portion of said openings;
    detecting far field diffracted light produced by said illumination of said first portion;
    illuminating a second portion of said openings, said second portion of said openings having a pattern which is substantially identical to said first portion;
    detecting far field diffracted light produced by said illumination of said second portion; and
    comparing signals detected from illumination of said first portion with signals detected from illumination of said second portion, thereby determining whether variations exist in said openings.

11. The method of claim 10, wherein the film is a dielectric layer on a semiconductor wafer.

12. The method of claim 11, wherein the openings are vias or contact holes in the dielectric layer.

13. The method of claim 10, wherein the first portion is a first die on a semiconductor wafer and wherein the second portion is a second die on the semiconductor wafer.

14. The method of claim 10, wherein detecting far field diffracted light produced by the illumination of the first portion or the second portion comprises detecting the diffracted light proximate a Fourier plane.

15. The method of claim 10, wherein detecting far field diffracted light produced by the illumination of the first portion or the second portion comprises detecting multiple orders of diffracted illumination.

16. An apparatus for evaluating the condition of topological features on a substrate surface, the apparatus comprising:
    a light source arranged to direct light onto the substrate surface such that the light is diffracted by the substrate surface;
    a sensor configured to capture and transmit a diffraction pattern of the light diffracted by the substrate surface; and
    a computer configured to compare the diffraction pattern from the substrate surface with a baseline diffraction pattern of light diffracted from a baseline surface having a condition corresponding to an expected condition of the substrate surface.

17. The apparatus of claim 16, further comprising optics aligned to capture light diffracted from the substrate surface and direct it onto the sensor.

18. The apparatus of claim 16, further comprising:
    a memory device for storing the baseline diffraction pattern, the memory device being coupled to the computer or being a component of the computer.

19. The apparatus of claim 18, wherein the memory device is a database storing a plurality of baseline diffraction patterns for multiple expected conditions of the substrate surface.

20. The apparatus of claim 16, wherein the light source is a coherent light source.

21. The apparatus of claim 20, wherein the light source is a laser.

22. The apparatus of claim 16, wherein the sensor is a camera.

23. The apparatus of claim 16, wherein the sensor is a charge coupled device or a photodiode array.

24. The apparatus of claim 1, further comprising a Fourier filter oriented to block one or more regions of the diffraction pattern from the substrate surface.

25. The apparatus of claim 1, further comprising optics comprising a microscope for providing views of the substrate surface.

26. The apparatus of claim 1, wherein the apparatus is configured to image only a portion of the diffracted light, which portion is sensitive to a particular surface condition.

27. A method for analyzing the condition of a surface of an electronic device, the surface having a defined pattern, the method comprising:
    (a) illuminating a first region of the surface such that light is diffracted off of features the surface;
    (b) filtering diffracted light to block one or more portions of a diffraction pattern from the substrate surface which portions contain little or no information pertaining to a surface feature of interest, while passing diffracted light containing information relevant to the surface feature of interest;
    (c) detecting the filtered diffracted light; and
    (d) comparing the filtered diffracted light to a baseline diffraction pattern of light diffracted from a baseline region having a condition corresponding to an expected condition of the surface feature of interest.

28. The method of claim 27, further comprising:
    (e) determining whether the detected light diffracted from the first region significantly deviates from the baseline diffraction pattern.

29. The method of claim 27, wherein the filtered diffracted light produces a spatial image which is detected.

* * * * *